United States Patent [19]

Wolfe

[11] 4,120,294

[45] Oct. 17, 1978

[54] ELECTRODE SYSTEM FOR ACQUIRING ELECTRICAL SIGNALS FROM THE HEART

[76] Inventor: Donna L. Wolfe, 32511 Sea Island Dr., Laguna Niguel, Calif. 92677

[21] Appl. No.: 718,017

[22] Filed: Aug. 26, 1976

[51] Int. Cl.² .............................................. A61B 5/02
[52] U.S. Cl. .......................... 128/2.05 T; 128/2.05 R; 128/2.06 F
[58] Field of Search ............... 128/2.05 A–2.05 Z, 128/2 H, 2 K, 2 P, 2.1 A, 2.1 E, 2.1 Z, 419 S, DIG. 4, 411, 2.06 A, 2.06 E, 2.06 F

[56] References Cited

U.S. PATENT DOCUMENTS

| | | | |
|---|---|---|---|
| T912,010 | 7/1973 | Holsinger | 128/2.06 E |
| 3,450,133 | 6/1969 | Birch, Jr. | 128/2.06 E |
| 3,772,874 | 11/1973 | Lefkowitz | 58/50 R |
| 3,807,388 | 4/1974 | Orr et al. | 128/2.05 T |
| 3,826,246 | 7/1974 | Raddi et al. | 128/2.06 B |
| 3,868,947 | 3/1975 | Holsinger | 128/2.06 E |
| 3,889,163 | 6/1975 | Symmes | 128/419 S |
| 3,983,690 | 10/1976 | McClintock | 58/50 R |
| 4,009,708 | 3/1977 | Fay, Jr. | 128/2.05 P |

OTHER PUBLICATIONS

Schaudinischky, L. et al., "Technical Note: The Shape Conforming Electrode," Med. & Biol. Engr., 7, 1969, pp. 341–343.

*Primary Examiner*—Robert W. Michell
*Assistant Examiner*—Francis J. Jaworski
*Attorney, Agent, or Firm*—Tilton, Fallon, Lungmus & Chestnut

[57] ABSTRACT

A wristband having inner and outer sensing electrodes capable of acquiring signals from bipolar limb leads and being electrically associated with electronics capable of processing such signals in a form representative of the electrical activity of the heart. The inner electrode is in continual electrical contact with the skin of the wrist upon which the band is worn. The outer electrode is isolated from the inner electrode and includes an outer portion exposed for contact by the fingers of the wearer's opposite hand. When such finger contact with the outer electrode is made, the bipolar circuit is completed and the ECG skin potential signals are sensed at the electrodes. The signals are processed to produce a digital indication of heartbeat rate, or other signal representative of heart activity.

15 Claims, 4 Drawing Figures

ELECTRODE SYSTEM FOR ACQUIRING ELECTRICAL SIGNALS FROM THE HEART

BACKGROUND

Many biologic, especially electrical, parameters are measured by the difference in electrical potential across specific organs or organ systems. Specifically, electrocardiograms (ECG) and other electrical parameters of cardiac activity require two or more electrodes or sensing devices placed so that they are on each side of the electrical axis of the heart. The basic arrangement, known as Lead I, consists of strapping an electrode to each wrist so as to measure the electrical potential difference across the heart. While such an arrangement is perfectly acceptable for clinical testing, it is inconvenient and impractical, if not impossible, in other circumstances such as during routine exercise programs.

A growing number of individuals are performing exercise programs regularly or intermittently. It is generally acknowledged that the heart rate is the best indicator of the value of such exercise to the cardiovascular system, i.e., when enough effort is expended to be useful and when so much effort is expended as to be dangerous. Thus, as reported in L. R. Zohman, Exercise Your Weight to Fitness and Heart Health, 16–18 (CPC International, 1974), it is important in an effective exercise training program that there be a gradual increase in heart rate until a target rate of 70 to 85 percent of the maximum attainable rate (depending on age and physical condition) is achieved. A period of 20 to 30 minutes of exercise at the target level will then provide a significant conditioning effect on the cardiovascular system. While the average target zones for different age groups are readily available (for an average 40-year old male it is, for example, 128 to 155 beats per minute), it is apparent that most individuals lack the skill or inclination to take their own pulse at various intervals during the exercise period to ascertain whether their heartbeat rate falls within the target range.

The difficulties and inconveniences attending the attachment of bipolar electrodes to the wrists or to other spaced points on opposite sides of the heart and the obvious problems in exercising with such electrodes in place have lead others to pursue the development of mechanical devices for sensing the pulse and then converting the mechanically-sensed pulse to an electrical signal for processing and display. U.S. Pat. No. 3,807,388, for example, discloses a heartbeat rate monitor in the form of a wrist-watch having a transducer mounted in the wrist strap to detect the pressure change (pulses) and convert them to electrical signals.

Apart from the fact that differences sometimes exist between pulse rate and true heartbeat rate, substantial problems exist in providing a transducer which is easily positioned for proper operation and which is capable of accurately sensing the pulse for any of a variety of users. Therefore, despite the availability of technology and electrical hardware for processing and displaying in digital form the pulse rate of a patient once that pulse has been detected by a suitable pressure transducer, devices in wristwatch form or in other convenient portable form have not achieved widespread use or substantial commercial availability.

Other patents illustrative of the art are U.S. Pat. Nos. 3,863,626, 3,802,698, 3,948,250, 3,586,835, and 3,717,140. Reference may also be had to V. Elings et al, A Cardiotachometer which Calculates Rate Digitally, IEEE Transactions on Biomedical Engineering, 468–470 (November, 1973), and Hartley, Analogue-Display Rate Meter Build Around Digital Switching Elements, Medical and Biological Engineering, 107–108 (January, 1976).

SUMMARY

An important aspect of this invention lies in the discovery that the problems of detecting differences in electrical potential across the heart as a direct indication of heart activity, in a manner convenient enough to use by someone wishing to check heartbeat rate during an ordinary exercise program, or desiring to display and/or transmit his electrocardiogram, may be achieved by locating both of the skin electrodes upon only one of the wearer's wrists and by constructing the wristband so that one of the two electrodes remains in electrical contact with the skin of that wrist. The other electrode, which is exposed along the outer surface of the band (either the strap itself or a casing supported by the strap) remains quiescent until such time as the wearer touches that electrode with the other hand. Such contact completes the circuit with the inner electrode in contact with the wrist and the outer electrode in contact with the fingers of the other hand. The electrical ECG signals picked up by the electrodes are then processed and displayed or transmitted utilizing any of a variety of known circuit arrangements and components. In one convenient form, the band includes a casing which contains all of the circuit elements (other than the electrodes) and digital display means such as light-emitting diodes for visually presenting heart rate in beats per minute. Alternatively it may be desirable to develop and/or transmit a signal representative of Lead I of the electro-cardiogram for such purposes as obtaining advice regarding medicines taken for disordered heart rhythms; evaluating the effect of treatment in certain heart disorders; and/or evaluating the function of a cardiac pacemaker. When transmission, such as over a telephone, is employed it is possible for professional medical evaluation to be made at a remote location, thereby saving time and increasing convenience.

Further objects, advantages, and embodiments of the invention will appear from the drawings and specification.

DRAWINGS

DESCRIPTION

Figure 1:
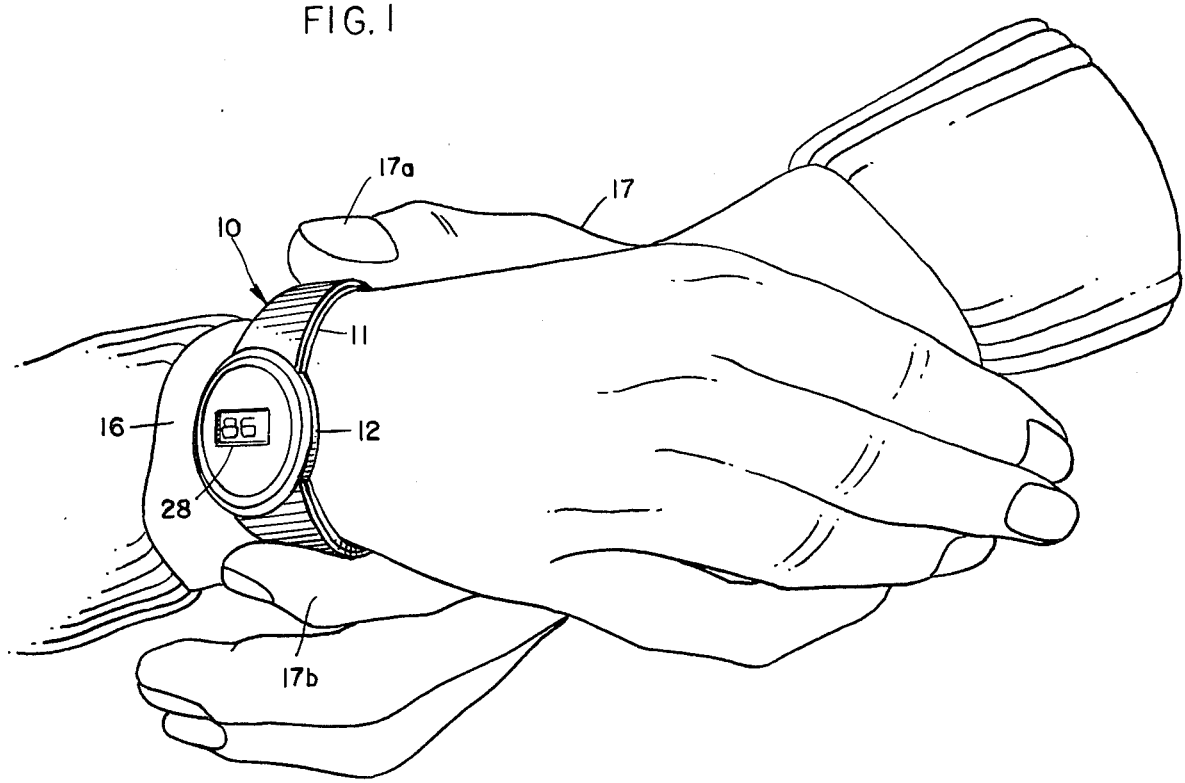
FIG. 1 is a perspective view of a heartbeat rate indicator embodying the invention, the indicator being illustrated as it is being used to display heartbeat rate in beats per minute.
Figure 2:
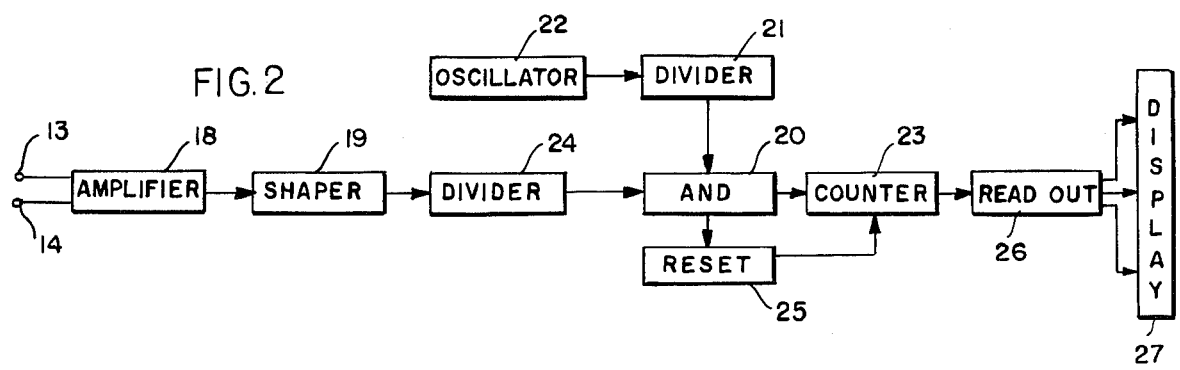
FIG. 2 is a simplified block diagram of the heartbeat rate monitor.
Figure 3:
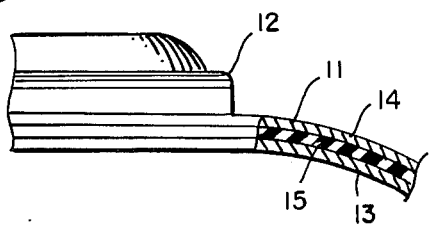
FIG. 3 is a fragmentary elevational view taken partly in section and showing the electrode construction of the heartbeat rate indicator.

Referring to FIGS. 1–3, the numeral 10 generally designates a heartbeat rate indicator in the form of a wristband having a strap 11 and a casing 12. The strap has electrically-conductive inner and outer layers 13 and 14 separated by an electrically-insulating central layer 15. When worn on the wrist, in the manner generally depicted in FIG. 1, only the conductive inner layer 13 is in contact with the wrist. Both the outer layer 14 and the casing 12, which may be in electrical contact with each other, are electrically isolated from the inner layer 13 and from the wearer's wrist 16.

The conductive inner layer 13 serves as one electrode of a bipolar electrode system, the other electrode of the system being outer layer 14. As shown in FIG. 1, the strap is of sufficient width so that its exposed outer surface may be easily contacted by the fingers of the wearer's other hand 17 without at the same time causing direct contact between those fingers and wrist 16. In the illustration given, the band is shown as it is being squeezed gently between the thumb 17a and index finger 17b and, although such a procedure helps assure effective electrical contact between the inner electrode and wrist 16, and between the outer electrode and fingers 17, it is to be understood that other fingers 17 might be used to contact the outer surface of the band or that, if desired, only a single finger, such as index finger 17b, might be used for that purpose. An important aspect of the invention is that it forces a wearer to hold his arms fixed during the measurement so as to remove artifacts, such as muscle movement, that might cause error.

The electrical circuitry for the heartbeat rate indicator may be similar to that disclosed in U.S. Pat. No. 3,807,388, or in other references previously identified. As diagrammatically depicted in FIG. 2, electrical signals detected by electrodes 13 and 14 are supplied to a sensing circuit including amplifier 18 and transmitted by way of shaper circuit 19 to an AND gate 20 to which a signal derived from divider 21 and oscillator 22 is also supplied. The oscillator may be crystal-controlled for operating at 16.384 kHz, and the divider circuit 22 may supply an output signal of 0.5 Hz. The output signal of divider circuit 21 may also, if desired, be supplied to a binary coded decimal to decimal decoder, to provide an output for display of seconds and, by way of a further divider circuit, to other decoders for the display of minutes and hours, respectively (not shown) where it is desired that the wristband indicator display time as well as heartbeat rate. Specific reference is made to U.S. Pat. No. 3,807,388 for such a modification.

For a lost or gained pulse from divider 21 to be insignificant, the frequency of the signal supplied by the divider to gate 20 should be, for example, 100 times the fastest heartbeat rate of say 150 beats per minute, so that the frequency required is about 250 pulses per second. To derive such a signal the divider 21 can be intercepted at the appropriate point to give an output of 256 pulses per second, this signal being supplied to the gate 20. The output of the gate 20 is supplied to an accumulating counter 23, the number of pulses at the minimum heartbeat rate of say 30 pulses per minute determining the capacity of the counter 23.

To reduce the possibility of occasional random heartbeat periods being displayed, it is preferable for the output of the shaper circuit 19 to be divided in frequency by a divider 24 being supplied to the gate 20 so as to average the measurement over several heartbeat periods. This requires a corresponding increase in the capacity of the counter 23. A further output of the gate 20 is connected to a reset circuit 25 which resets the counter 23 at the end of each counting period. The number of pulses counted in each counting period varies inversely with the heartbeat rate and hence a suitable readout circuit 26 may be provided to give signals corresponding to 100's, 10's, and units of heartbeat rate for supplying to an array 27 of light-emitting diodes. Upon completion of the circuit in the manner depicted in FIG. 1, the light-emitting diodes display the wearer's heartbeat rate in beats per minute through window 28. It will be understood, of course, that other display means such as liquid crystals might be used.

The method of use of the device is believed apparent from the foregoing. The wearer simply places the wristband device on his wrist 16 before commencing an exercise program, a sports activity, or any other activity for which heartbeat rate monitoring is desired. By attaching the device to his wrist 16, the user pre-positions inner electrode 13 in direct electrical contact with one limb, that is, a part of the body on one side of the electrical axis of the heart. Completion of the circuit does not take place, however, until the user, desiring to obtain a visual digital indication of his heartbeat rate, touches the outer electrode 14 of the same wristband with a finger (or fingers) of his other hand. The effectiveness of the electrical contact is improved by slight pressure, as already described, and is further enhanced by perspiration developed as a result of the physical activity involved.

Figure 4:
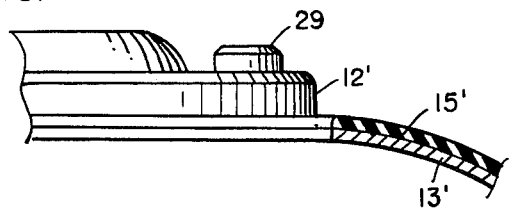
FIG. 4 is a view similar to FIG. 3 but depicting another embodiment of the invention.

The embodiment illustrated in FIG. 4 is similar to the one already described except that the outer electrode takes the form of a conductive push button 29 carried by the casing portion 12' of the wristband device. The inner electrode 13' is similar to previously-described electrode 13, and an insulating layer 15' extends over electrode 13' to insure that the inner electrode contacts no portion of the wearer's body other than wrist 16. In addition to serving as the second electrode of the bipolar electrode system, button 29 may be arranged to actuate a switch when depressed to couple the power source to the display circuits, which may include light-emitting diodes, only when the wearer desires a readout.

While in the foregoing an embodiment of the invention has been disclosed in considerable detail for purposes of illustration, it will be understood by those skilled in the art that many of these details may be varied without departing from the spirit and scope of the invention.

I claim:

1. An electrode system for sensing heart activity comprising a wristband adapted to be worn on the wrist of one hand and having inner sensing electrode means directly engagable with such wrist; insulating barrier means extending over said inner sensing electrode means for shielding the same against contact with any part of the wearer's body except said wrist; outer sensing electrode means carried by said wristband and electrically isolated from said inner electrode means by said insulating barrier means; said inner and outer sensing electrode means being disposed on oppositely-facing sides of said wristband with said barrier means interposed between said inner and outer sensing electrode means; said outer sensing electrode means being exposed and adapted for selective contact by the fingers of the wearer's other hand; and sensing circuit means disposed in said wristband in electrical circuit with said inner and outer electrode means for sensing electrical signals derived therefrom that are representative of the electrical activity of the wearer's heart.

2. The electrode system of claim 1 in which there is measuring circuit means disposed in said wristband and responsive to said sensing circuit means for measuring heart activity.

3. The electrode system of claim 2 in which there is display circuit means disposed in said wristband and responsive to said measuring circuit means for generating a visual signal representative of the electrical activity of the heart.

4. The electrode system of claim 3 in which said measuring circuit means measures heartbeat rate and said display circuit means generate a visual signal representative of heartbeat rate.

5. The electrode system of claim 4 in which said wristband includes a casing containing said sensing, measuring, and display circuit means and providing a face for the visual display of said heartbeat rate.

6. The electrode system of claim 5 in which said outer electrode sensing means comprises an electrically-conductive finger button projecting from said casing.

7. The electrode system of claim 4 in which said display circuit means provides a digital display of heartbeat rate in beats per minute.

8. The electrode system of claim 7 in which said display circuit means includes light-emitting diodes.

9. The electrode system of claim 7 in which said display circuit means includes liquid crystals.

10. The electrode system of claim 4 in which said measuring circuit system includes time-based signal generating means and means responsive to both said sensing circuit means and said time-based signal generating means for generating a signal representative of heart activity.

11. The electrode system of claim 1 in which said outer electrode sensing means comprises an outer electrically-conductive layer of said wristband extending a substantial extent along the circumference of said wristband.

12. A method for determining heart activity, comprising strapping a first cardiac electrode directly against the wrist of one hand of a wearer by a wristband which also provides an exposed second electrode supported out of contact with said wrist and in electrically-isolated relation with respect to said first electrode, said first and second electrodes being in circuit with means for processing bioelectrical signals from said electrodes and for providing a measurement of heart activity, said wearer thereafter touching said second electrode with at least one finger of the other hand to complete the electrical circuit, whereby, said first electrode is in direct electrical contact with a limb on one side of the electrical axis of the heart and the second electrode is in electrical contact with a limb on the other side of the heart's electrical axis.

13. The method of claim 12 in which said means for processing bioelectric signals from said electrodes includes means carried by said wristband for displaying a visual indication of heartbeat rate, whereby, upon touching said second electrode with at least one finger of said other hand to complete the electrical circuit, a signal representative of heartbeat rate is generated and visually displayed.

14. The method of claim 12 in which said step of touching said second electrode with at least one finger of the other hand includes immobilizing said hands relative to each other, thereby eliminating artifacts that might otherwise be generated by hand movement.

15. The method of claim 12 in which said step of touching said second electrode involves firmly gripping said wristband between a pair of fingers of said other hand to place said fingers in firm electrical contact with said second electrode and simultaneously urge said first electrode into tight electrical contact with the wrist of said one hand.

* * * * *